United States Patent [19]

Kajiyama et al.

[11] Patent Number: 5,352,598
[45] Date of Patent: Oct. 4, 1994

[54] PURIFIED LUCIFERASE FROM LUCIOLA LATERALIS

[75] Inventors: Naoki Kajiyama, Noda, Japan; Tsutomu Masuda, Needham, Mass.; Hiroki Tatsumi, Noda; Eiichi Nakano, Iwatsuki, both of Japan

[73] Assignee: Kikkoman Corporation, Noda, Japan

[21] Appl. No.: 759,814

[22] Filed: Aug. 29, 1991

Related U.S. Application Data

[63] Continuation of Ser. No. 332,978, Apr. 4, 1989, abandoned.

[30] Foreign Application Priority Data

Apr. 12, 1988 [JP] Japan ................................. 63-88246

[51] Int. Cl.$^5$ ......................... C12N 9/02; C12N 1/00
[52] U.S. Cl. .................................. 435/189; 435/243; 435/815; 435/816
[58] Field of Search ................ 435/189, 243, 815, 816

[56] References Cited

U.S. PATENT DOCUMENTS 4,581,335  4/1986  Baldwin ........................... 435/172.3

FOREIGN PATENT DOCUMENTS 273889    7/1988   European Pat. Off.
0301541   2/1989   European Pat. Off.
WO87/03304 6/1987  PCT Int'l Appl.
WO88/00617 12/1988 PCT Int'l Appl.

OTHER PUBLICATIONS

Filippova et al., Biochemistry, 44, pp. 1508–1513, 1980.
Chem. Abs. 69(15):59203w (1968).
Chem. Abs. 110(13):109122g (1989).
Shimomura et al, (1977), *Proc. Nat. Acad. Sci.*, 74:2799–2802.
Kricka et al. (1982), *Arch. Biochem. Biophys.*, 217:674–681.
Wienhausen et al. (1985), *Photochem. Photobiol.*, 42:609–611.
*Methods in Enzymology*, 133:3–15 (1986).
Esaki, et al., Iconographia Insectorum Japonicorum, 1st ed., Hokuryukan, Tokyo, Japan, 1932.
Berezin, et al., (1977), Biological Chemistry, vol. 3, No. 12, pp. 1–39, translation.
T. Fukushi, Biomedical Research 3 (5), pp. 534–540, "Isolation and Translation of Renin mRNA From The Mouse Submandibular Gland" (1982).
T. Masuda et al., Argic. Biol. Chem., 50 (2), pp. 271–279, "Synthesis of Enzymatically Active Mouse Submandibular Gland" (1986).
N. N. Ugarova et al., Enzyme Microb. Technol., vol. 4, pp. 224–228, "Immobilization of luciferase from the firefly Luciola mingrelica–catalytic properties and stability of the immobilized enzyme" (Jul. 1982).

*Primary Examiner*—Douglas W. Robinson
*Assistant Examiner*—Michael V. Meller
*Attorney, Agent, or Firm*—Banner, Birch, McKie & Beckett

[57] ABSTRACT

A purified luciferase from *Luciola lateralis* is disclosed. The enzyme is characterized by having properties including: an optimum pH range of 7.5 to 9.5, an optimum temperature range of 0° C. to 50° C., and that the enzyme does not act on ADP, CTP, UTP, and GTP. The enzyme is purified by using a process which includes: gel filtration chromatography, hydroxyapatite column chromatography, and a tris(hydroxy)aminomethane-hydro-chloric acid buffer.

1 Claim, 1 Drawing Sheet

PURIFIED LUCIFERASE FROM LUCIOLA LATERALIS

This application is a continuation of application Ser. No. 07/332/978, filed Apr. 4, 1989, now abandoned.

BACKGROUND OF THE INVENTION

Field of the Invention and Related Art Statement

This invention relates to a luciferase which catalyzes the oxydation of luciferin by an oxygen molecule.

Since luciferase derived from *Luciola lateralis* is unstable, its purification has heretofore been unsuccessful (Tanpakushitsu Kakusan Koso (Protein, Nucleic Acid, Enzyme) Vol. 32, No. 10, p. 44–59, particularly p. 47 (p. 1234-1249, particularly p. 1237), (1987)).

Luciferases are very effectively usable, for example, for quantitating ATP.

SUMMARY OF THE INVENTION

The present invention is intended to provide luciferase derived from *Luciola lateralis*.

In consideration of the conditions described above, the present inventors earnestly investigated and consequently succeeded in isolating luciferase from the posterior portion of *Luciola lateralis*, whereby the present invention has been accomplished.

That is, the present invention is a luciferase having the following physico-chemical properties:

① Action

The luciferase is an enzyme which catalyzes the oxidation of luciferin by an oxygen molecule, as shown by the enzymic reaction formula:

Luciferin + ATP + $O_2$ ⟶

Oxyluciferin + AMP + Pyrophosphoric acid + $CO_2$ + light

② Substrate specificity

The luciferase does not act on ADP, CTP, UTP and GTP.

③ Optimum pH, and pH range for stability

The optimum pH is 7.5–9.5 when luciferin is used as a substrate (see FIG. 1).

The stable pH range of the enzyme is 6.0–10.5 (see FIG. 2).

④ Range of temperature suitable for action

0°–° C.

⑤ Conditions of inactivation by pH, temperature, etc.

At pH's of 5.0 or lower and 12.0 or higher, the luciferase is completely inactivated after 4 hours' exposures under such a condition as mentioned above.

At pH 7.8, the luciferase is completely inactivated by heat treatment at a temperature of 55° C. for 15 minutes.

⑥ Thermal stability

After being treated at a temperature of 40° C. for 15 minutes, the luciferase has a residual enzymic activity of 78.3%. Even after being treated at a temperature of 50° C. for 8 minutes, the luciferase has a residual enzymic activity of 6%.

DETAILED DESCRIPTION OF PREFERRED EMBODIMENTS

The present invention is explained below in detail.

First, physico-chemical properties of the present enzyme are described below.

① Action

The enzyme catalyzes the oxidation of luciferin by an oxygen molecule, as shown by the enzymic reaction formula:

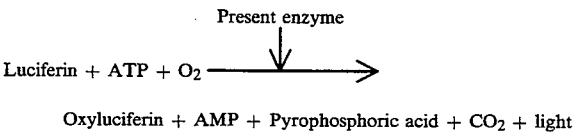

Luciferin + ATP + $O_2$ ⟶

Oxyluciferin + AMP + Pyrophosphoric acid + $CO_2$ + light

② Substrate specificity

The enzyme does not act on ADP, CTP, UTP and GTP.

③ Optimum pH, and pH range for stability

Figure 1:
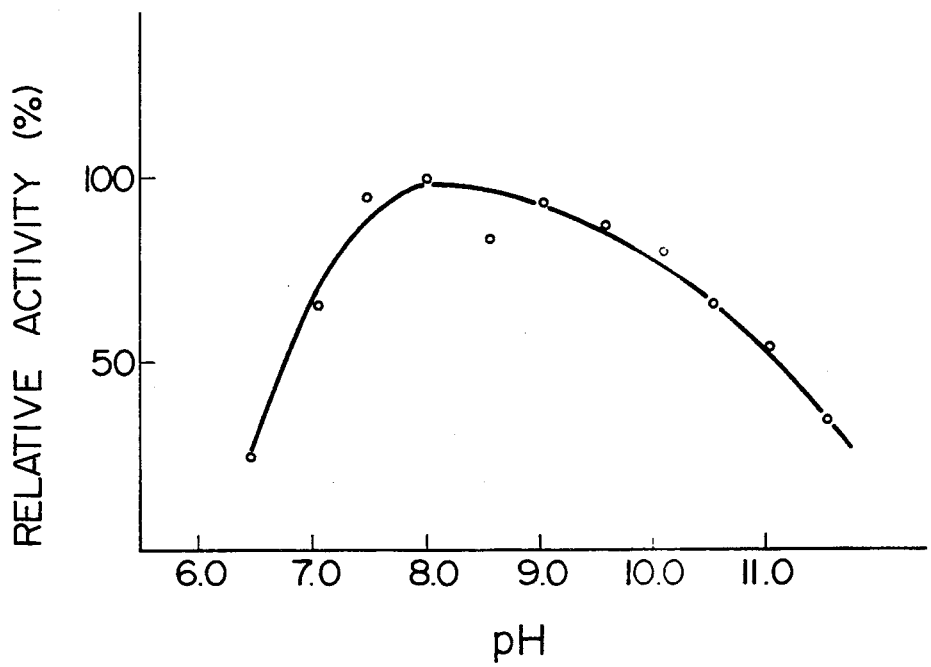
FIG. 1 is a graph showing the optimum pH region of the enzyme of the present invention.
Figure 2:
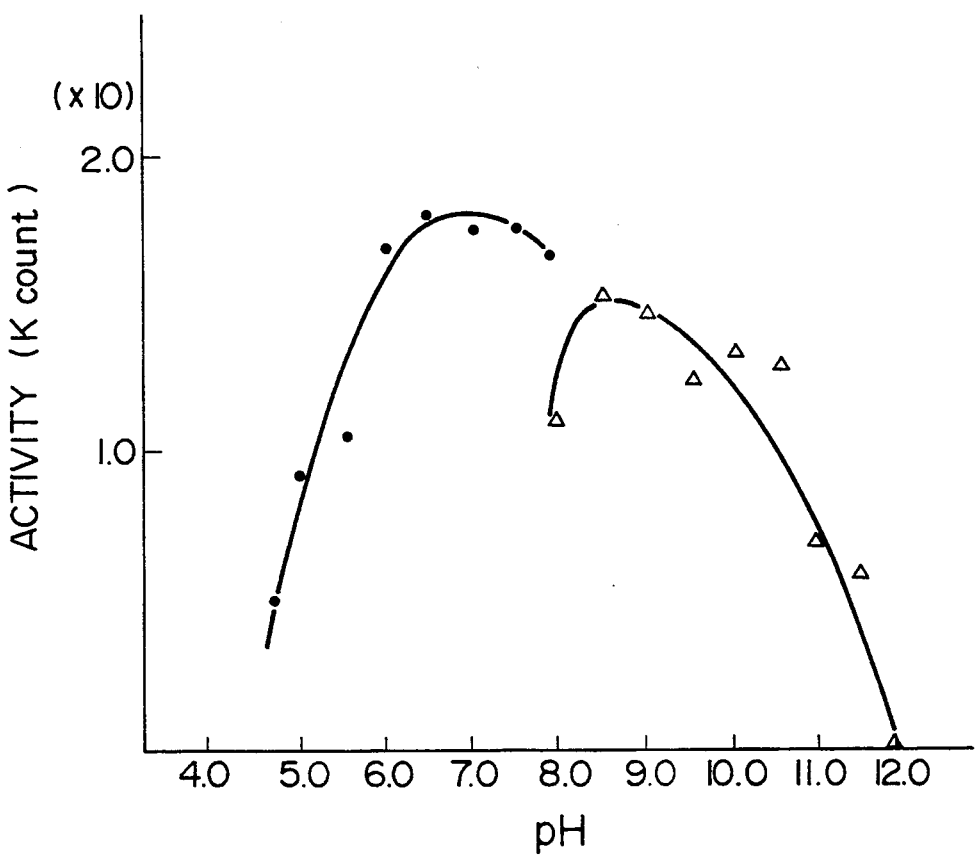
FIG. 2 is a graph showing the pH range for stability of the enzyme of the present invention.

The optimum pH is, as shown in FIG. 1, 7.5–9.5 as measured by carrying out the reaction by the use of luciferin as a substrate at various pH's of 25 mM glycylglycine buffer solution of 6.5 to 11.5 and at a temperature of 30° C., and measuring the quantity of light (the number of photons) emitted in 20 seconds. The stable pH range of the enzyme is, as shown in FIG. 2, 6.0–10.5 as measured by adding the enzyme to each of buffer solutions (25 mM phosphate buffer solutions (pH 4.6–8.0) and 25 mM glycine.sodium chloride-sodium hydroxide buffer solutions (pH 8.0–11.5), each of which contains ammonium sulfate to 10% saturation) containing luciferin, and allowing the enzyme to act at a temperature of 0° C. for 4 hours. In FIG. 2, ●—● and △—△ show the activity in the case of using the 25 mM phosphate buffer solutions and the activity in the case of using the 25 mM glycine.sodium chloride-sodium hydroxide buffer solutions, respectively.

④ Measurement of titer

A luciferin mixed solution is prepared by mixing 8 ml of 25 mM glycylglycine buffer solution (pH 7.8), 0.5 ml of a magnesium sulfate solution (a solution prepared by adding magnesium sulfate to 25 mM glycylglycine buffer solution (pH 7.8) to a magnesium sulfate concentration of 0.1 M) and 0.8 ml of a luciferin solution (a solution prepared by adding luciferin to 25 mM glycylglycine buffer solution (pH 7.8) to a luciferin concentration of 1 mM).

Into a mixture of 400 μl of the luciferin mixed solution thus obtained and 10 μl of luciferase to be assayed is poured 80 μl of an ATP solution (a solution prepared by adding ATP to 25 mM glycylglycine buffer solution (pH 7.8) to an ATP concentration of 10 mM). Simultaneously with the pouring, the number of photons generated is measured by adding up for 20 seconds by means of a luminometer (LUMINESCENCE READER BLR-201, mfd. by ALOKA CO., LTD.).

(5) Range of temperature suitable for action

When the reaction is carried out at pH 7.8 and at each temperature and the quantity of light (the number of photons) emitted in 20 seconds is measured, the suitable temperature for action ranges from 0° to 50° C.

(6) Conditions of inactivation by pH, temperature, etc.

(a) Conditions of inactivation by pH

At pH's of 5.0 or lower and 12.0 or higher, the enzyme is completely inactivated after 4 hours.

(b) Conditions of inactivation by temperature

At pH 7.8, the enzyme is completely inactivated by heat treatment at a temperature of 55° C. for 15 minutes.

(7) Heat resistance

After 100 μl of a solution (60 mM phosphate buffer solution (pH 7.5) containing 10% (V/V) ethylene glycol, 0.1 M NaCl and 0.2% (W/V) albumin) containing 100K count of a purified preparation of the enzyme was maintained at a temperature of 40° C. for each of 15, 30 and 60 minutes, the residual enzymic activity was measured. The results obtained are shown in Table 1.

For comparison, in Table 1 are also shown the results of measuring the residual activities of luciferases of *Luciola cruciata* and *Photinus pyralis* in the same manner as described above.

TABLE 1

| | Kind of luciferase Residual activity of luciferase (%) | | |
|---|---|---|---|
| Maintenance time (min) | Luciola lateralis (the invention) | Luciola cruciata (reference) | Photinus pyralis (reference) |
| 15 | 78.3 | 38.8 | 33.7 |
| 30 | 70.6 | 19.5 | 19.0 |
| 60 | 48.2 | 5.3 | 6.0 |

It can be seen that as is clear from Table 1, the present invention is a luciferase which is much superior to the reference luciferases in heat resistance.

Next, a concrete means for preparing the present enzyme is described below.

For preparing the present enzyme, any method may be employed. For example, the following method can be exemplified.

As *Luciola lateralis* used in the present invention, there may be used any of that collected from the natural world, that artificially cultivated, etc. This species is widely distributed over Amur, the Kuriles, Hokkaido, Hoshu, Shikoku and Kyushu and is the most common firefly in Japan. Since a large amount of luciferase exists in the posterior portion of *Luciola lateralis*, said posterior portion is suitable as a source from which luciferase is separated.

*Luciola lateralis* is added to a buffer solution and ground to obtain a ground product.

As the buffer solution, any one can be used so long as it does not inactivate luciferase, and there may be exemplified, for example, solutions prepared by adding ammonium sulfate to each of tris(hydroxy)-aminomethane-hydrochloric acid buffer solutions, glycine-sodium chloride-sodium hydroxide buffer solutions, phosphate buffer solutions, etc. to 10% saturation.

As the means for the grinding, there may be exemplified, for example, a method using a mortar and a pestle, and methods using a homogenizer, a Waring blender, a French press, or the like.

Subsequently, the residue is removed from the ground product by usual centrifugation, filtration, or the like to obtain a crude enzyme solution. If necessary, the crude enzyme is treated by a method properly selected from freeze-drying, alcohol precipitation, acetone precipitation, etc., to obtain crude enzyme powder.

A purified enzyme preparation can be obtained from the crude enzyme solution or the crude enzyme powder by a combination of methods properly selected from the group consisting of, for example, gel filtration methods using Sephadex, Ultrogel, Bio-Gel, etc.; adsorption-and-elution methods using ion exchangers; electrophoretic methods using polyacrylamide gels, etc.; adsorption-and-elution methods using hydroxyapatite; sedimentation methods such as sucrose gradient centrifugation, and the like; affinity chromatographic methods; and fractionation methods using a molecular sieve membrane, a hollow-fiber membrane, etc.

EXAMPLE

The present invention is further illustrated with the following example.

EXAMPLE

To 25 mM tris(hydroxy)aminomethane-hydrochloric acid buffer was added 1 mM disodium ethylenediaminetetraacetate and 2 mM phenylmethylsulfonyl fluoride, followed by adding thereto ammonium sulfate to 10% saturation. To 15 ml of the mixed solution (pH 7.8) thus obtained was added the posterior portions of 200 insects (*Luciola lateralis*) (purchased from Seibu Department Store Co., Ltd.), and destroyed by means of PHYSCO-TRON (mfd. by NITI-ON Medical and Physical Instrument Manufacturing Company LTD.). The liquid thus obtained was centrifuged at 12,000 r.p.m. for 20 minutes to obtain 14.5 ml of a supernatant (a crude enzyme solution).

The crude enzyme solution thus obtained was subjected to salting-out by the use of ammonium sulfate by a conventional method, and the precipitate formed at 30 to 70% saturation as centrifuged at 30,000 r.p.m. for 10 minutes. The resulting precipitate was dissolved in a 25 mM mixed solution (a solution (pH 7.8) prepared by adding 1 mM disodium ethylenediaminetetraacetate and ammonium sulfate in such an amount that 10% saturation therewith was effected, to a small amount of 25 mM tris(hydroxy)aminomethane-hydrochloric acid buffer) to obtain a solution.

Subsequently, this solution was subjected to gel filtration chromatography by passing the same through an Ultrogel AcA 34 (mfd. by Pharmacia K. K.) column equilibrated with the above 25 mM mixed solution, to obtain an activity fraction.

The fraction thus obtained was dialyzed against a phosphate buffer solution (a buffer solution prepared by adding 0.1 M sodium chloride and 10% (V/V) of ethylene glycol to a 10 mM sodium hydrogenphosphate-sodium dihydrogenphosphate solution). The dialyzed solution was adsorbed on a hydroxyapatite HPLC (TSK gel HA-1000, mfd. by Toyo Soda Mfg. Co., Ltd.) column equilibrated with 10 mM phosphate buffer, and linear gradient elution with phosphate buffer solutions (pH 7.5) ranging in concentration from 10 to 100 mM was carried out to obtain 180 μl (enzymic activity: $2.4 \times 10^2$ K count) of a purified luciferase activity fraction derived from *Luciola lateralis*.

What is claimed is:

1. A purified luciferase from *Luciola lateralis* characterized as follows:
   (a) action:
      said luciferase is a purified enzyme which catalyzes the oxidation of luciferin by an oxygen molecule, as shown by the enzymatic reaction formula:
      luciferin + ATP + $O_2 \rightarrow$ oxyluciferin + AMP + pyrophosphoric acid + $CO_2$ + light
   (b) substrate specificity:
      said luciferase does not act on ADP, CTP, UTP and GTP;
   (c) optimum pH, and pH range for luciferase stability:
      the optimum pH is 7.5 to 9.5 when luciferin is used as a substrate, and the stable pH range is 60 to 10.5;
   (d) optimum temperature range for activity:
      0° to 50° C.;
   (e) conditions of inactivation by pH, temperature;
      at pH of 5.0 or lower and 12.0 or higher, said luciferase is completely inactivated when it is exposed to such a condition for four hours,
      at pH 7.8, said luciferase is completely inactivated by heat treatment at a temperature of 55° C. for 15 minutes;
   (f) thermal stability:
      after being treated at a temperature of 40° C. for 15 minutes, said luciferase has a residual enzymatic activity of 78.2%; even after being treated at a temperature of 50° C. for 8 minutes, said luciferase has a residual enzyme activity of 6%.
   said purified luciferase having the purity of luciferase purified from *L. lateralis* by:
   dissolving the precipitate formed at 30 to 60% ammonium sulfate saturation from crude *L. lateralis* luciferase enzyme solution in a solution prepared by adding ethylenediaminetetraacetate to 1 mM and ammonium sulfate to 10% to 25 mM tris(hydroxy)aminomethane-hydrochloric acid buffer, pH=7.8;
   subjecting said dissolved precipitate solution to gel filtration chromatography and recovering the active fraction;
   dialyzing said active fraction against a buffer solution prepared by adding 0.1 M sodium chloride and 10% (V/V) ethylene glycol to a 10 mM sodium hydrogen phosphate-sodium dihydrogenphosphate solution;
   absorbing said dialyzed fraction on a hydroxyapatite column equilibrated with 10 mM phosphate buffer; and
   collecting the fraction having luciferase activity eluted from said hydroxyapatite column by a linear gradient from 10 to 100 mM phosphate buffer, pH=7.5.

* * * * *